United States Patent [19]

Huang

[11] 4,327,073
[45] Apr. 27, 1982

[54] AUTOMATED METHOD FOR QUANTITATIVE ANALYSIS OF BIOLOGICAL FLUIDS

[76] Inventor: Henry V. Huang, 232 S. Catalina, Pasadena, Calif. 91106

[21] Appl. No.: 138,182

[22] Filed: Apr. 7, 1980

[51] Int. Cl.³ .................. G01N 33/54; G01N 33/56; G01N 33/58; G01N 35/00
[52] U.S. Cl. .................. 424/1; 23/230 B; 23/230.3; 23/915; 23/920; 422/66; 424/8; 424/12; 435/7
[58] Field of Search ............ 422/66; 23/230 B; 435/7; 424/1

[56] References Cited

U.S. PATENT DOCUMENTS

| | | | |
|---|---|---|---|
| Re. 28,339 | 2/1975 | Maxon | 422/66 X |
| 3,260,413 | 7/1966 | Natelson | 422/66 X |
| 3,526,480 | 9/1970 | Findl | 422/66 |
| 3,645,852 | 2/1972 | Axen | 424/12 X |
| 3,675,488 | 7/1972 | Viktora | 422/66 X |
| 3,952,091 | 4/1976 | Grunberg | 23/230 B |
| 4,071,315 | 1/1978 | Chateau | 422/66 X |

Primary Examiner—Sidney Marantz
Attorney, Agent, or Firm—Fischer, Tachner & Strauss

[57] ABSTRACT

A method for the simultaneous and rapid quantitative analysis of biological fluids for a plurality of substances, each of which undergoes at least one reaction with a respective cognate compound. Typical substances include hormones, enzymes, and viruses. The method comprises binding each of a plurality of the respective reactive compounds onto a preselected area of a substrate carrier; e.g., to a band or spot on a carrier film and exposing the sensitized carrier to a sample of the biological fluid to permit the unknown substances contained therein to react with their respective cognate compound which is immobilized on the carrier and then removing excess of the sample from the carrier and developing the carrier and measuring the concentration of the reaction products that are at preselected areas of the carrier. The method permits the entire analysis to be automated and a sample such as a blood serum sample to be analyzed for a host of components such as enzymes, hormones, or viruses in a simple, direct and standardized procedure.

17 Claims, 7 Drawing Figures

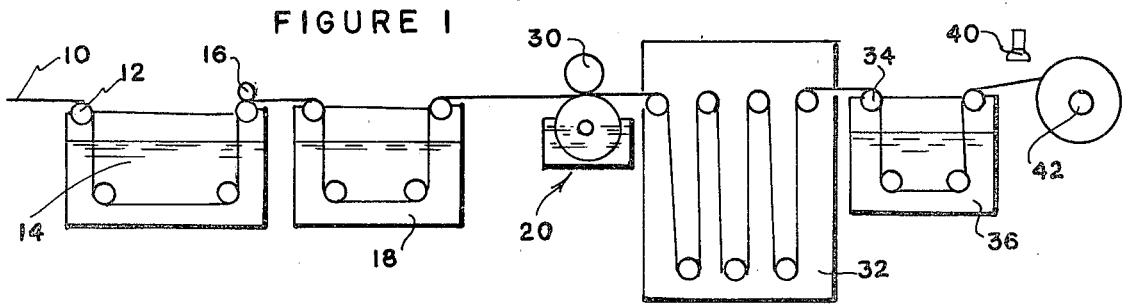
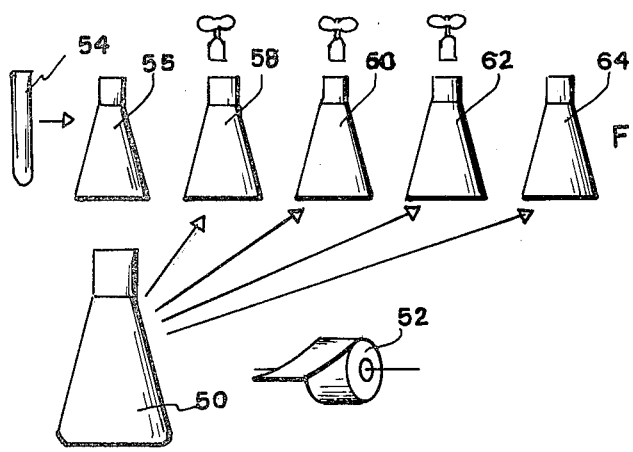
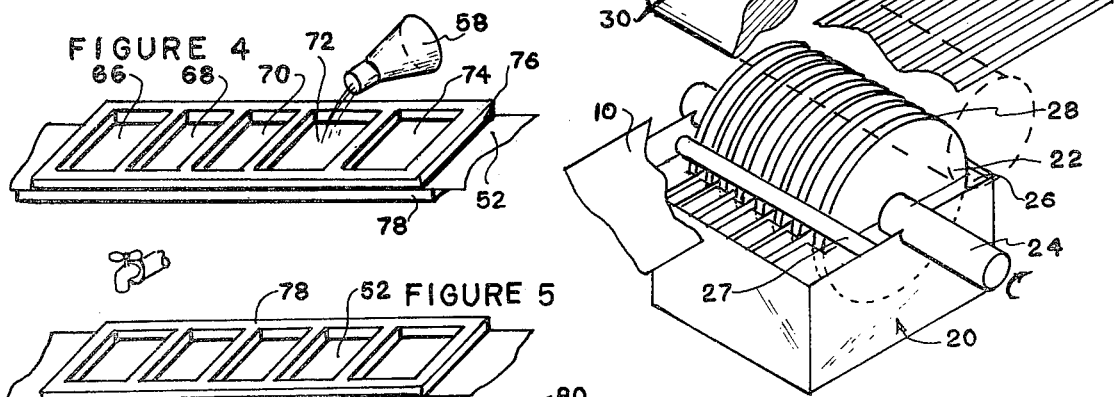
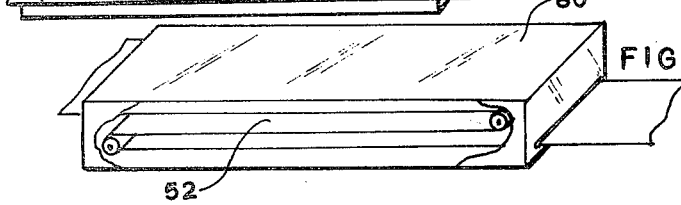
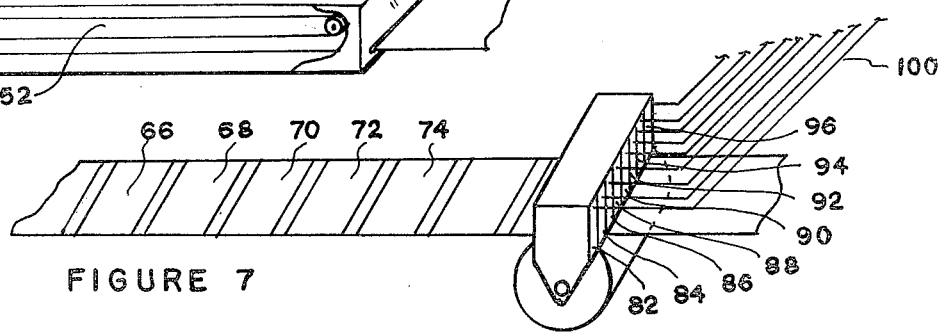

AUTOMATED METHOD FOR QUANTITATIVE ANALYSIS OF BIOLOGICAL FLUIDS

BACKGROUND OF THE INVENTION

1. Field of Invention

This invention relates to clinical assays of biological fluids and, in particular, to a standardized method for such analysis.

2. Brief Statement of the Prior Art

The analysis of biological samples such as spinal fluid, blood serum, urine, saliva, etc. for components such as enzymes, hormones, and viruses is a highly complex procedure. Recent advancements have provided for the mass analysis of a sample of biological fluids for a host of unknown substances; however, this procedure requires individual treatment of samples for each of the unknown substances determined and utilizes relatively complex and costly instrumentation.

Several analytical procedures have been developed for the analysis of biological fluids including radioimmunoassay and enzyme-linked immunosorbent assay. These methods employ tracer-labelled substances in a direct or competitive assay. In the direct method, the unknown substance forms a reaction conjugate with the tracer-labelled reactant and then the subsequent assay will determine the concentration of the tracer bonded to the unknown substance. In the competitive procedure, the tracer-labelled substance competes with the unknown substance of the sample for conjugation with a known quantity of a reactive compound. The concentration of the tracer-labelled substance in the conjugated product reflects its concentration and the concentration of the unlabelled, unknown substance. In the enzymatic assay, the conjugated enzyme is analyzed, typically by exposing the material to a chromogenic substrate to yield a chromophore which is analyzed by fluoroscopic or colorimetric methods and in the radioassay, a radioactive element labelled reactive compound is analyzed by radioactive counters.

While the aforementioned analytical procedures provide an elegant and precise analysis of biological fluids, vastly superior to previous bioassays, the procedures are quite complex and require costly instrumentation.

BRIEF STATEMENT OF THE INVENTION

The invention provides a method for the simultaneous analysis of a plurality of unknown substances in biological clinical samples for which cognate compounds are available. The method is applicable to immune systems in which peptide or non-peptidal hormones conjugate with their respective antibodies and nonhormonal substances such as drugs, viruses, enzymes, serum proteins, and other materials form conjugates with their respective antibodies, as well as nonimmune systems in which hormones or nonhormonal substances form conjugates with materials such as specific binding proteins in plasma, or other receptors. The method is practiced by immobilizing the reactive compound, such as the antibody, binding protein, or receptor, or conversely, the drugs, viruses, enzymes or serum proteins, onto preselected areas of a substrate carrier. The carrier can be a plate or continuous film strip which is derivitized with a functional group to provide a covalent bonding site for bonding to the reactive compound or to a ligand that bonds to the reactive compound. Also, the substrate can be an ion exchange material or an adsorbent that provides non-covalent bonding to the reactive compound. The resultant carrier thus has a plurality of immobilized reactive compounds at preselected areas; e.g., at bands or spots and the thus sensitized carrier is exposed to a sample of the biological clinical sample to permit the unknown substances of the sample to react with their respective immobilized cognate compounds. The method contemplates a competitive analysis, in which a tracer-labelled substance is added to the biological sample prior to exposure, or a direct assay in which the unadulterated sample is contacted with the sensitized substrate carrier. Thereafter, the exposed substrate carrier is washed or freed of any excess of the sample and developed and the preselected areas are analyzed to detect the concentration of the conjugated substances. This determination is facilitated by calibration of the sensitized carrier by exposing preselected calibration areas of the sensitized carrier to a plurality of dilutions of the standard solution of tracer-labelled substances. The entire assay can be completely automated using combinations of standard solutions and sensitized carriers for any of a plurality of clinical assays.

BRIEF DESCRIPTION OF THE DRAWINGS

The invention will be described with reference to the drawings, of which:

FIG. 1 is a schematic illustration of the preparation of the carrier and immobilized reactive compounds;

FIG. 2 illustrates the applicator station of FIG. 1; and

FIGS. 3-7 illustrate, schematically, the clinical use of the invention.

DESCRIPTION OF PREFERRED EMBODIMENTS

The method comprises the simultaneous assay of biological fluids for a plurality of substances. Substances which can be analyzed by the method include peptide and nonpeptidal hormones, viruses, enzymes, serum proteins, tumor antigens, drugs, cyclic nucleotides, intrinsic factor, complementary DNA, etc. In brief, any congeneric substance of a biological fluid which specifically reacts with a specific cognate reactive compound can be included as a substance for analysis by the method of the invention. The following table summarizes some of the substances which occur in biological samples and which can be analyzed in accordance with the invention:

TABLE 1 BIOGENIC SUBSTANCES

PEPTIDE HORMONES

Pitutary Hormones

Growth hormone
Adrenocorticotropic hormone (ACTH)
Melanocyte stimulating hormone (MSH)
Glycoproteins, thyroid simulating hormone (TSH), follicle simulating hormone (FSH), and luteinizing hormone (LH)
Prolactin
Lipotropin (LPH), vasopresin, oxytocin

Chorionic Hormones

Human chorionic gonadotropin (HCG)
Human chorionic somatomammotropin (HCS)

Pancreatic Hormones

Insulin

Proinsulin
C-peptide
Glucagon

Calcitropic Hormones

Parathyroid hormone (PTH)
Calcitonin (CT)

Gastrointestinal Hormones

Gastrin
Secretin
Cholecystokinin-pancreozymin (CCK-PZ)
Enteroglucagon
Vasoactive intestinal polypeptide (VIP)
Gastric inhibitory polypeptide (GIP)

Vasoactive Tissue Hormones

Angiotensins
Bradykinins

Hypothalamic Releasing Factors

Thyrotropin releasing factor (TRF)
Gonadotropin releasing factor (GnRF)
Growth hormone release inhibiting factor (GHIF)

NONPEPTIDAL HORMONES

Thyroidal Hormones

Triiodothyronine
Thyroxine

Prostaglandins

Steroids

Aldosterone
Corticosteroids
Estrogens
Androgens
Progesterones

NONHORMONAL SUBSTANCES

Drugs
Cardiac glycosides
Morphine
LSD
Barbiturates
Chlorpromazine
Nicotine
Penicillin and Gentamicin
D-tubocurarine

Cyclic Nucleotides

Adenosine 5'-monophosphate (cAMP)
Guanosine 5'-monophosphate (cGMP)
Inosine 5'-monophosphate (cIMP)
Unidine 5'-monophosphate (cUMP)

Enzymes $C_1$ esterase
Fructose 1,6 diphosphatase
Plasminogen and Plasmin
Chymotrypsin
Trypsin
Carbonic anhydrase isoenzymes

Virus

Hepatitis B antigen

Tumor Antigens

Carcinoembryonic antigen
alpha-Fetoprotein

Serum Proteins

Thyroxin binding globulin
IgG, IgE
Properdin
Fibrinogen
Anti-Rh antibodies

Other Substances

Intrinsic factor
Rheumatoid factor
Hagerman factor
Folic acid
Neurophysine
Calcium binding protein
Stephylococcal
beta-Enterotoxin Specific antibodies for each of the preceding are known and available compounds. These antibodies are commonly identified by combining the prefix "anti" with the name of the biogenic substance, e.g., anti-growth hormone, anti-insulin, anti-calcitonin, anti-thyroxine, etc. These antibodies are the specific cognate reactive compound as used in this invention.

Many biogenic substances also react in non-immune systems with binding proteins or receptors and enzymes react with their specific substrates. The invention is also applicable to such nonimmune systems for analysis of these biological substances.

The following table summarizes some of these substances and their respective reactive compounds:

TABLE 2

| BIOGENIC SUBSTANCE | REACTIVE COMPOUND |
|---|---|
| HORMONES | |
| Thyroxin | Thyroxin binding protein |
| Cortisol | Cortisol binding protein |
| Corticosterone | Corticosterone binding protein |
| Cortisone | Cortisone binding protein |
| II-deoxycortisol | II-deoxycortisol binding protein |
| Progesterone | Progesterone binding protein |
| Testosterone | Testosterone binding protein |
| ACTH | ACTH receptor |
| Angiotensin | Angiotensin receptor |
| Calcitonin | Calcitonin receptor |
| Catecholamines | Catecholamine receptors |
| Gonadotropins | Gonadotropin receptors |
| Growth hormone | Growth hormone receptor |
| Insulin | Insulin receptor |
| Oxytocin | Oxytocin receptor |
| Prolactin | Prolactin receptor |
| TSH | TSH receptor |
| Thyrotropin-releasing hormone (TRH) | TRH receptor |
| NONHORMONAL SUBSTANCES | |
| Intrinsic factor | Vitamin $B_{12}$ |
| FA reductase | Folic Acid |
| Phosphodiesterases | cAMP, cGMP |
| Messenger RNA | Complementary DNA |
| ENZYMES | |
| Galactosidase | 3-chloro-4-bromoindole-beta-D-galactoside |
| Glucosidase | 3-chloro-4-bromoindole-beta-D-glucoside |
| Phosphatase | 3-chloro-4-bromoindole-beta-D-phosphate |
| Sulfatases | P-nitrophenylsulfate |
| Esterases | p-nitrophenylacetate |
| N-acetylglucosamidase | p-nitrophenyl-N-acetyl-$\beta$-D- |

TABLE 2-continued

| BIOGENIC SUBSTANCE | REACTIVE COMPOUND |
|---|---|
| | glucosaminide |
| γ-glutamyl transpeptidase | L-glutamyl-p-nitroanilide |
| Proteases (trypsin) | α-N-benzoyl-DL-arginine-p-nitro anilide |
| β-glucuronidase | naphthol AS Bl-D-glucuronic acid (7-bromo-3-hydroxy-2-naphth-9-anisidide-D-glucuronic acid) |

TABLE 3—BONDED REACTIVE COMPOUND

L-Alanine
Aminobutyric acid
L-Arginine
L-Asparagine
L-Aspartic acid
Cycloleucine
L-Cystine
L-Glutamic acid
L-Glutamine
Glycine
Hemoglobin
L-Histidine
L-4-Hydroxyproline
L-Isoleucine
L-Leucine
L-Lysine
L-Methionine
L-Ornithine
L-Phenylanine
L-Proline
L-Pyroglutamic aicd
L-Serine
L-Threonine
L-Tyrosine
L-Valine
N-Acetyl-D-galactosamine
N-Aceyl-D-glucosamine
N-Acetyl-D-mannosamine
D-Fructose
L-Fucose
D-Galactosamine hydrochloride
D-Galactosamine
D-Galactose
D-Glucosamine hydrochloride
D-Glucose
L-Glucose
Lactose
D-Mannosamine hydrochloride
D-Mannose
Albumin (bovine serum)
N-acetylated Concanavalin A
Insulin
L-Thyroxine
Wheat germ agglutinin
NUCLEOSIDES
Adenosine
Cytidine
Deoxyadenosine
Deoxyuridine
Guanosine
Thymidine
Uridine
Adenosine 3-,5-cyclic phosphate, ammonium salt
Adenosine 5-diphosphate, trisodium salt
Adenosine 5-triphosphate, tetrasodium salt
Cyclic AMP
Cyclic GMP
Deoxycytidine 5-monophosphate, diammonium
Deoxyguanosine 5-triphosphate, tetrasodium salt
Deoxyribonucleic acid
Polyadenylic acid, sodium salt
Poly(deoxyadenylate-deoxythymidylate)
Polyuridylic acid, sodium salt
Ribonucleic acid
Thymidine 5-triphosphate, tetrasodium salt
Adenine
Adenine hydrochloride
Bromouracil, 5-
Hypoxanthine
Thymine
Uracil
Corticosterone
Digitoxin
Digoxin
Dihydroprogesterone
Dihydrotestosterone
Estradiol
Estriol
Estrone
Progesterone
Testosterone
Dansyl chloride
Dinitrofluorobenzene, 2,4-
Histamine
Ethylenediamine dihydrochloride
Horseradish peroxidase The substrate which is used for immobilizing the functional reactive compound in the invention can be selected from a wide variety of substrates. Briefly, a substrate having a functional group can be used for covalent bonding of the functional reactive compound or the substrate can have ion exchange sites for ionic bonding of the functional reactant. Another suitable substrate can be an adsorbent in which the reactive compound is attracted or bonded by Van der Waals bonding. The substrate can be in varied physical forms, although a continuous film strip of the substrate is a desirable form for ease of handling. Other forms are also useful; e.g., the particulate or granular substrates can be physically bonded or embedded in a gel coating on a film strip or solid plate or, can be physically confined between a pair of plates which can have sufficient permeability to permit the solids to be contacted by the sample and developing solutions.

A preferred substrate for use in the invention is a carbohydrate; e.g., lactose, sucrose, starch, cellulose, etc. Of these, it is preferred to employ the polysaccharides such as starch and cellulose. Derivatives such as the ethers and esters of the polysaccharides also can be used for their physical and chemical properties; e.g., hydroxyethyl cellulose, carboxymethyl cellulose, cellulose acetate, etc. The preparation of gels and films of polysaccharides is a well-known and established practice and can be employed in the invention to obtain a continuous film of the substrate carrier; e.g., a cellulose acetate film or can be used to obtain a gel coated strip; e.g., a plastic or paper film coated with a gelatinized starch, or a paper strip can be used directly.

The carbohydrates can be used in the invention by reaction with cyanogen bromide to synthesize imidized carbohydrates. The reaction can typically be performed to incorporate from 1 to about 3 imido groups per carbohydrate molecule and it commonly cross-links carbohydrate molecules with acyclic imidocarbonates. Cyclic imidocarbonate groups are also formed at reoccurring positions along the carbohydrate chain. The imido groups react readily with amino groups of the reactive substances, e.g., amino groups of a binding protein, antibody or receptor, or of the drug, virus, serum protein or enzyme. This class of cyanogen bromide activated carbohydrates is commercially available from various suppliers, including Pharmacia Fine Chemicals Inc., 800 Centennial Avenue, Piscataway, N.J.

Another class of useful substrates for the carrier are the anionic and cationic polyelectrolytes. These materials are polyionic macromolecules obtained by the polymerization of functional monomers to provide recurring cationic or anionic groups along the polymer chain. Examples of these polyelectrolytes are polyvinyl ammonium chloride, poly-4-vinyl-N-methylpyridinium bromide, potassium polyacrylate, polyvinylsulfonic acid, etc. The preparation of these materials is well known and established in the art and the products are commercially available in a variety of forms. The polyelectrolytes can be incorporated into membranes by adsorption or by physical occlusion by addition of the polyelectrolyte to the polymerization of a film forming resin such as ethylene, vinyl acetate, vinyl chloride, etc., and mixtures thereof. Alternatively, a film of a functional monomer such as acrylic acid with film forming co-monomers such as ethylene, vinyl acetate, vinyl chloride, methylacrylate, etc. When the poly electrolytes are cross-linked by co-polymerization with a cross-linking co-monomer such as di-vinyl benzene, the resultant solid is the commonly recognized ion exchange resin and the polyelectrolyte can be used in this form, also. In this form, the resin can be incorporated in a membrane by physically admixing the powdered resin with the film forming resin; e.g., a polyvinyl chloride resin, or can be incorporated into a thin film by any of the techniques disclosed herein for obtaining a thin film of a granular substrate on a suitable carrier plate.

Other ion exchange solids which can be used in the invention include the inorganic ion exchange solids such as clays, and natural and synthetic zeolites. These inorganic ion exchange solids are crystalline alumino silicates characterized by lattice-layered structure having hydroxyl groups at edges and corners to provide ion exchange sites for the clay structures and rigid three-dimensional crystalline structures for the zeolites. The zeolites possess channels and cages and possess a net charge that is balanced by cations within the channels and cages, thereby imparting the ion exchange capability. The inorganic ion exchange solids can be obtained in a finely subdivided state; e.g., from a size range having an average particle diameter of 0.1 micron to ⅛ inch for spherical particles, and for extrudates, diameters up to about ⅛ inch. Preferably, for use in the invention the ion exchange solids are used in a fine degree of subdivision, typically having a size range from about 1 to about 100 microns average particle diameter. These ion exchange solids can be formed in a thin film by incorporating the solids in a gel; e.g., a gelatinized starch, and then coated onto the surface of a carrier plate or flexible strip of paper or plastic film. Alternatively, the finely subdivided solids can be physically confined between parallel plates of glass, carbon, or plastics such as polystyrene, polycarbonates, and the like. These plates can be provided a sufficient degree of permeability to fluid flow to permit access of the treating solutions to the solids.

Other solids useful as the substrate include adsorbents such as silica, activated carbon, alumina, hydrox apatite, polystyrene, etc. These adsorbents have a particular affinity for certain proteins; e.g., proteins readily bond to polysytrene by adsorption; nucleic acid and other proteins bond to hydrox apatite. The solid adsorbents, as the solid ion exchange substrates, can be formed into a thin film by physical confinement between parallel plates or by adhesively bonding to a carrier substrate.

As previously mentioned, the preferred substrate for use in the invention is cyanogen bromide activated carbohydrate and a suitable commercially available material is Agarose. This substance is known to bond the reactive compounds set forth in Table 3.

Also, as previously mentioned, the reactive substances can be bonded directly by reaction of their amino groups with the imidocarbonates of the cyanogen bromide treated carbohydrate. In some cases, however, it is preferred to first react the imidocarbonate groups with an excess quantity of a long chain alpha, omega-diamine, e.g., 1,7-diaminoheptane. This results in a substrate having free amino groups spaced from the surface by long carbon chains. The amino groups are free to react with carboxylic acid groups of the reactive substance. This avoids steric hinderance of the vital functional group of the reactive substance or, in some cases, avoids reaction between the imidocarbonate and the site of the vital functional group of the reactive substance.

The preparation of the substrate carrier and the immobilized reactive compound is shown schematically in FIGS. 1 and 2. FIG. 1 illustrates preparation of a substrate carrier and the immobilization of reactive compounds onto preselected areas of the carrier. A continuous strip 10 of a high wet-strength paper of filter grade quality is passed over roller 12 and into a cold alkaline buffered aqueous bath of a solution of cyanogen bromide in vessel 14. The film is removed through squeeze rollers 16 and is passed through a cold buffered aqueous bath 18 to rinse excess, unreacted cyanogen bromide.

The resultant paper strip has a surface bearing reactive cyclic and acyclic imidocarbonate groups. The strip 10 is then treated to deposit continuous bands of preselected reactive compounds at station 20, illustrated in greater detail in FIG. 2.

As shown in FIG. 2, station 20 has a banding applicator formed of a plurality of wheel applicators 22. Each wheel applicator is rotatably supported on shaft 24, above its respective reservoir 26 of an aqueous solution of a reactive compound. Each wheel has a porous rim 28 formed of a sponge-like material which is saturated with the reactive compound solution in reservoir 26. A squeeze roller can be provided as shown at 27 to remove excess of the solution of the reactive compound before contacting the strip 10. The wheel applicators transfer the solutions of the reactive compounds onto the strip 10 as continuous bands as strip 10 passes between wheel applicators 22 and pressure roller 30. In a typical embodiment, strip 10 can be 1.5 inches wide and eight bands, each ⅛ inch wide can be applied, each band separated from the adjacent bands by untreated bands approximately 1/16 inch wide.

The treated paper strip 10 is then passed through an incubation chamber 32 (FIG. 1) where it is maintained at an appropriate temperature, e.g., 20° C., for sufficient time, e.g., 10–45 minutes to permit the reactive compounds to bond to the reactive sites of the carrier. The strip 10 is then passed over roller 34 and into bath 36 where excess, unreacted quantities of the reactive compounds are removed. The resultant, sensitized carrier strip 10 can then be dried by heating with lamp 40 and accumulated on spool 42 as a roll for packaging and distribution to a clinic or laboratory.

The method is applicable to use of tracer-labelled substances which can be used in direct or competitive assays. It is thus applicable to use of radioactive tracer labelled substances including the following radioactive tracer elements of phosphorous, carbon, hydrogen, sulfer, or iodine;

$$^{32}P, \; ^{14}C, \; ^{3}H, \; ^{35}S, \; ^{125}I, \text{ and } ^{131}I$$

The tracer elements are incorporated in the biochemical substances by in vivo labeling or by use of reactive reagents containing the radioactive element and these reactive reagents are readily available. An example of a suitable radioactive reagent is iodinated p-bydroxyphenylpropionic acid, N-hydroxysuccinimide ester. The reagent is available with the $^{125}I$ isotope and is highly reactive for bonding to polypeptide antigens such as TSH, insulin, and hGH, as well as a wide variety of proteins. Other examples of radioactive tracer-labelled reagents that can be used are tritium labelled reactive substances.

Biogenic substances can be readily labelled with tritium with any of several techniques. The most commonly used technique is catalytic reduction of an unsaturated or halogenated substance with tritium gas. Substances which have other reducible groups such as acids, esters, nitriles, etc., can be selectively reduced without loss of these groups by reduction with a metal hydride such a tritium-labelled sodium borohydride which is effective in the selective reduction of aldehyde and ketone groups of biogenic substances. When it is desired or necessary to introduce tritium into a substance without loss of any reducible group, tritium can be exchanged for a hydrogen radical of the substance by a catalytic exchange reaction. In this reaction the substance is treated with tritium gas or tritium labelled water in a solvent such as acetic acid or dimethylformamide and in the presence of a noble metal catalyst. This treatment is particularly effective with substances having aromatic rings and has been used for tritium exchange in substances such as nucleosides, nucleotides, sugars and amino acids. Another technique that has been used to introduce tritium into biogenic substances is to place the substance in a closed receiver filled with tritium gas and place the receiver in an ionizing field for a prolonged period, e.g., several weeks.

Radioactive iodine, $^{125}I$ or $^{131}I$, can also be introduced into biogenic substances by iodination with radioactive iodide salts in the presence of solvents such a p-toluenesulfonchloramide. This technique has been used to lable albumins, globulins, angiotensins and glucagon with radioactive iodine.

Enzymes can also be used as the tracer in a tracer-labelled system. One of the most widely used enzymes for a tracer is horseradish peroxidase. This enzyme will react with a chromophore such as 4-chloro-1-naphthol in the presence of an oxidizing agent such as hydrogen peroxide to precipitate a blue-to-purple solid. Other useful enzymes in a tracer system are alkaline phosphatase which will react with alpha-naphthol compounds in the presence of diazonium salts to precipitate a red-to-violet solid. Another suitable enzyme for use as a tracer is lactate dehydrogenase which will precipitate an insoluble blue solid from tetrazolium. The following chromophores have been coupled to biogenic substances and the resultant derivatives cleaved by an enzyme reactive for the particular substance to produce a colored product: 5-bromo-4-chloroindolyl derivatives, naphthol dye derivatives, 4-methylumbelliferyl derivatives, nitrophenyl derivatives, and nitroanilide derivatives.

Fluorescent compounds such as rhodamine, DANSYL, fluorescamine, fluorescein, dichlorotriazinylaminofluorescein (DTAF), and tetramethylrhodamine isothiocyanate (TRITC) can be used as immunoglobulins to provide fluorescent tracer-labelled substances which are useful in practice of the invention.

The method of the invention is conveniently practiced in a competitive assay. In this procedure, a standard solution containing known concentrations of tracer-labelled substances; e.g., tracer-labelled hormones, is added to the sample of biological clinical fluid to be analyzed. When the substrate carrier having the immobilized reactive compounds is exposed to the resultant mixture, the tracer-labelled hormones compete with their unlabelled hormones of the biological fluid for conjugated tracer-labelled substance which adheres to the substrate carrier depends on the concentrations of the labelled and unlabelled substances. Since the former is known, the latter can be readily determined by detection and comparison of the detected value to calibrated areas on the substrate carrier. The calibrated areas on the carrier are obtained by exposing preselected calibration areas of the carrier to a mixture of the standard solution of the tracer-labelled substance and dilutions of a known quantity of the unlabeled substance; e.g., one-tenth, one-hundredth, and one-thousandth dilutions of a known-content solution.

In some assays, tracer-labelled substances are incompatible or undesirable. In these systems, the method is applied by exposing the sensitized substrate carrier with its immobilized reactive compound to a sample of a predetermined quantity of the biological fluid and washing the excess of the sample and substances from the exposed substrate carrier. Similarly, calibration areas of the sensitized substrate carrier are exposed to dilutions of a reference solution, containing known quantities of each of the substances to be analyzed, and the excess is washed away. Thereafter, the substrate carrier is developed for subsequent determination of the quantity of conjugated substance by exposing the substrate carrier bearing the conjugated substances to a standard solution of a tracer-labelled developer; i.e., a tracer-labelled reactive compound that will conjugate with the conjugated substances on the exposed substrate carrier. As an illustration, an immuno system is analyzed by using a substrate carrier bearing immobilized antibodies which conjugate with antigens of unknown quantities in the biological fluid. The exposed substrate carrier is then washed to remove excess, unconjugated antigens and is thereafter developed by further exposure to a standard solution of a specific tracer labelled antibody for the antigen, e.g., $^{125}I$-labelled antibody. After allowing sufficient time for the labelled antibody to conjugate with the antigen that is conjugated to the antibody bonded to the substrate carrier, excess of the developing tracer-labelled standard solution is drained and washed from the substrate carrier and thereafter the concentration of the conjugated antigen is determined by the radioactive counting techniques and comparison of the results with those of calibrated areas of the substrate carrier.

The same application can be made to a competitive assay by using a functional competing compound which is reactive in subsequent treatment with a labelled developer; i.e., a reactive compound having a detectable tracer element or group. As an example, the method can be applied to an immuno system by bonding an antibody; anti-immunoglobulin. The biological sample which contains an unknown quantity of the immunoglobulin is admixed with a standard solution of a competing substance; e.g., dinitrophenylated immunoglobulin. The substrate with the bonded antibody is exposed to the mixture of the sample and standard solution of competing substance and thereafter the excess quantity of the mixture is drained and the substrate is washed to remove any unconjugated labelled and unlabelled immunoglobulin. The resultant exposed substrate carrier is then further exposed to a standard solution of an antibody reactive with the conjugated immunoglobulin substances. An example of a suitable solution is a standard solution of peroxidase-coupled anti-dinitrophenylated immunoglobulin. After this exposure, the excess of the labelled antibodies standard solution is drained from the substrate carrier, the substrate carrier is washed and then treated in a bath of chromogenic peroxidase substrate which precipitates a colored solid in the presence of the peroxidase enzyme; e.g., the combination of 4-chloro-1-naphthol and hydrogen peroxide. The concentration of the precipitated color body is then detected using conventional colorimetric and light adsorption techniques.

The clinical application of the invention is illustrated schematically in FIGS. 3-7. As shown in FIG. 3, the clinic is provided with an analysis kit consisting of a standard solution 50 of tracer-labelled substances, a mixture of one each for each of the biogenic substances to be assayed in a serum sample, dilutions of a reference solution 58, 60, 62 of unlabelled substance a mixture of one each for each of the biogenic substances to be assayed for, and a strip 52 of a carrier having the immobilized reactive compounds arranged in bands, prepared as described with reference to FIGS. 1 and 2.

The serum sample 54 is admixed with a predetermined proportion of the standard solution, e.g., equal volumes, to prepare a test solution 55. The standard solution is then divided into four calibration solutions 58, 60, 62 and 64. The reference solutions are added as 10,100 and 1,000 fold dilutions in flasks 58, 60 and 62, respectively. The reference solutions are dilutions (10,100, and 1,000 fold) of a mixture of known quantities of each biogenic substance assayed for.

As shown in FIG. 4, the preselected areas 66, 68, 70, 72 and 74 of the substrate carrier strip 52 are then treated with one of the resulting solutions, i.e., 58, 60, 62 and 64, and the serum plus standard solution test solution 55. Various equipment can be used to limit the solutions to their preselected areas 66-74. A grid plate 76 with open areas corresponding to each of the areas can be placed over strip 52 resting on table 78 and the solutions such as 58 can be applied to the strip through the open grid areas. After permitting a sufficient time for competitive assay reaction between the immobilized reactive compounds and the labelled and unlabelled substances of the test solution and labelled substances of the calibration solutions, unreacted substances are drained and washed from the strip 52 as shown in FIG. 5.

The carrier strip 52 may then be processed or developed by further treatment, depending on the particular tracer which is used. If radioactive tracer labelled substances are used, no further development will normally be required and the strip is passed directly to the detection step shown in FIG. 7. If, however, chromophore labelled substances are used it may be necessary to incubate the strip 52 in chamber 80 shown in FIG. 6. Controlled reaction conditions of time and temperature and concentration of any developer solution, as needed, are maintained in chamber 80 for the formation and precipitation of the colored reaction product onto strip 52. Thereafter the strip is passed to the detection step, FIG. 7. The strip 52 has a plurality of transverse bands 66, 68, 70, 72 and 74 in which each of the longitudinal bands has a tracer concentration which is proportional to the ratio of the known concentration of the tracer labelled substance in the standard solution and the known concentration of the unlabelled substance in each calibration reference solution. The concentrations of substances assayed for in the test solution may then be determined from the resulting calibration curve.

The strip 52 can be processed automatically in the detection step, using a ganged array of sensing elements, 82, 84, 86, 88, 90, 92, 94 and 96 for each of the longitudinal bands on the strip such as radiation counters or photoelectric elements. For this purpose, the strip 52 can be passed over a pressure roller 98 positioned below the sensing elements. The output signals from the sensing elements are passed by conductors such as 100 to suitable signal processing equipment to determine the concentrations of each of the assayed substances in the serum sample.

The following specific examples will illustrate practice of the invention and demonstrate results obtainable thereby:

EXAMPLE 1

In this example, a human blood sample is processed to remove the blood cells and obtain a blood serum sample. It is desired to analyze the blood serum sample for a number of hormones and for his purpose, a hormone kit based on the invention is employed. The hormone kit comprises a standard solution of tritium-labelled hormones, hormone receptors, and hormone binding proteins for each of the unknowns, and a set of dilutions of reference solutions containing known quantities of each of the hormones, receptors and binding proteins to be analyzed in the blood sample. The substrate carrier is a film strip approximately two inches wide and having continuous, longitudinal bands approximately one-eighth inch in width of the specific antibodies for each of the hormones to be analyzed. The following table summarizes the substances of unknown concentration to be analyzed in the blood serum sample and the immobilized component of the substrate carrier:

TABLE 4

| Unknown Substance | Immobilized Component |
| --- | --- |
| thyroxin | anti-thyroxin |
| thyroxin binding protein | thyroxin |
| insulin | anti-insulin |
| glucagon | anti-glucagon |
| calcitonin receptor | calcitonin |
| testrosterone | anti-testrosterone |
| testrosterone binding protein | testrosterone |
| progesterone | anti-progesterone |
| progesterone binding protein | progesterone |
| estrogen | anti-estrogen |

TABLE 4-continued

| Unknown Substance | Immobilized Component |
|---|---|
| estrogen binding protein | estrogen |

In each case a known quantity of tracer-labelled substance to be assayed is included in the standard solution. A known quantity and unlabelled substance is similarly included in each of the reference dilutions.

The method is practiced by calibrating the substrate carrier by exposing successive transverse bands approximately one inch in width of the carrier strip to the standard solution at its full concentration mixed with 10, 100 and 1000 fold dilutions of the reference solution. The blood serum sample is admixed with an appropriate volume of the standard solution and a successive band, one inch in width, is treated with the resulting mixture. Several duplicate bands of the calibration mixtures and the blood serum-standard solution mixture are provided. After exposure of the film strip, the excess solutions are washed from the strip with several washings with a suitable buffer solution such as physiological saline solution. Thereafter, the film strip is passed beneath a radiation counter head assembly having a plurality of stacked radiation detector heads, each head arranged immediately adjacent and in the path of a respective longitudinal band on the film strip. The radiation counts determined from the bands of the film exposed to the mixture of the serum sample and standard solution are averaged and compared to the radiation counts of the calibrated areas, interpolating between the counts from the calibration areas to determine the concentrations of each of the ten components analyzed in the blood serum. By this procedure, a single sample of blood serum is prepared for exposure of the substrate carrier film, yet a total of ten unknown substances are analyzed.

EXAMPLE 2

In this example, a serum sample is analyzed for antibodies to each of the common flu viruses using a flu virus analysis kit of the invention. The analysis kit comprises a substrate carrier film approximately two inches in width and having 12 parallel, longitudinal bands approximately one-eighth inch in width of immobilized flu antigen for each of the viruses to be analyzed. The standard solution which is used in the analysis is a peroxidase-labelled anti-flu antigen for each of the respective flu viruses. The reference solutions are dilutions of known quantities of unlabelled antibodies to each of the flu viruses. The standard solution is admixed with the serum sample in appropriate volumetric proportions. Dilutions of 10, 100 and 1000 fold of the reference solution added to the standard solution. The film strip is then exposed in successive transverse bands to the standard solution and the mixture of the standard solution with 10, 100 and 1000 fold dilutions of the reference solution, and to the previously prepared volumetric mixture of the serum sample and standard solution. The film strip is exposed for three replicas and the exposed film strip is then washed to remove any excess of the exposure solutions. The film strip is then dipped into a bath of peroxidase substrate containing 4-chloro-1-naphthol and peroxide. The peroxidase oxidizes the substrate and precipitates a bluish purple color solid from the bath onto the film strip at a concentration proportional to the concentration of the peroxidase tracer in each of the calibration and sample areas. The film strip is removed from the bath of the peroxidase substrate, washed, and is then processed through a colorimeter. The film strip which is passed through the colorimeter has repeating sets of narrow, parallel color bands running along the length of the film strip with each short band having a color intensity proportional to the peroxidase tracer bonded in that band to the film strip. The colorimeter which is used has a plurality of parallel photosensitive detection heads preadjusted for maximum sensitivity in the light band characteristic of the preceipitated color body. The color determinations are a series of electrical signals of varied voltages proportional to the color intensity and the voltage signals generated from the bands of a sample area are compared to the voltage signals of the bands for the calibration areas and interpolated to provide an instantaneous determination of the presence and concentration of the anti-flu viruses in the serum sample.

The invention provides the advantage for the instantaneous and simultaneous determination of a wide plurality of different biogenic substances in a biological clinical fluid. The analysis is performed with a minimum of sample preparation and permits determination of a variety of biogenic substances with only a single sample preparation. The method also utilizes a single or common tracer and thus permits use of a simple instrument which utilizes common detectors and generates a plurality of compatible signals for comparison. The invention provides the capability of supplying small clinics with a complete biological fluid assay capability. The invention is utilized by preparing the film strips with the immobilized reactive components and the corresponding standard solution at a central laboratory for each of the commonly analyzed mixtures of biogenic substances; e.g., cold virus kits, flu virus kits, hormone kits, liver enzyme kits, etc. These standard solutions and the film strips can be preserved for prolonged shelf lives and can thus be prepackaged and delivered to clinics for storage and use as needed. Since all of the tracer-labelled substances can use a single common tracer, such as a single radioactive component; e.g., $^{125}I$, or a single tracer enzyme; e.g., peroxidase, the clinic need employ only a single analytical instrument which is versatile for all of the analyzed substances.

The invention has been described with reference to the illustrated and presently preferred embodiments. It is not intended that the invention be unduly limited by this disclosure of the preferred embodiments. Instead, the invention is intended to be defined by the means, reagents, steps, and their obvious equivalents set forth in the following claims.

What is claimed is:

1. A method for quantitative analysis of a biological fluid for a plurality of substances, each of which forms specific reaction conjugates with a respective reactive compound which comprises the steps of:
   (a) admixing said biological sample with a standard solution of tracer-labelled, known quantities of said substances;
   (b) contacting the resultant mixture of biological sample and standard solution with a sensitized substrate carrier having a plurality of said respective reactive compounds bonded onto preselected areas of an inert substrate carrier forming a substrate carrier sensitized at each of a plurality of preselected areas with a respective one of a plurality of immobilized reactive compounds interspaced by areas of said substrate carrier free of said compounds to permit said labeled and unlabeled substances contained in said mixture to competitively conjugate with their respective reactive compounds immobilized on said substrate carrier;

(c) washing excess of said sample from each of said preselected areas of said substrate carrier in a common washing treatment to obtain an exposed substrate carrier; and (d) measuring the concentration of said conjugated substances on the preselected areas of said carrier.

2. The method of claim 1 including the step of preparing the sensitized carrier by reacting each of a plurality of said respective reactive compounds with said carrier to bind each of said reactive compounds onto a preselected area of said carrier interspaced by areas of said substrate carrier free of said compounds.

3. The method of claim 1 including the steps for calibrating the sensitized carrier by exposing preselected calibration areas of said sensitized carrier to a plurality of dilutions of a reference solution mixed with said standard solution.

4. The method of claim 3 including the steps of comparing the detected tracer concentrations at preselected sample areas to the tracer concentrations detected at the preselected calibration areas to determine the concentration of said substances in said biological fluid.

5. The method of claim 4 wherein said tracer-labelled substances are radioactive derivatives of said substances.

6. The method of claim 4 wherein said tracer-labelled substances are enzymatic derivatives of said substances.

7. The method of claim 6 including a developing step by the simultaneous contacting of said plurality of preselected areas of said carrier, in a common contacting step, with a chromophore enzyme-substrate derivative to precipitate a chromogenic substance on said preselected areas from said chromopore enzyme-substrate derivative cleaved by said enzymatic derivative.

8. The method of claim 5 wherein said tracer-labelled substances are chromophore derivatives of said substances.

9. The method of claim 8 wherein said chromophore derivatives are fluorophores.

10. A method for quantitative analysis of a biological fluid for a plurality of substances, each of which forms specific reaction conjugates with a respective reactive compound which comprises the steps of:

(a) admixing said biological sample with a standard solution of known quantities of competing compounds which functionally compete with said substances in said biological fluid in the formation of reaction conjugates with said reactive compounds;

(b) contacting the resultant mixture of biological sample and standard solution with a sensitized substrate carrier having a plurality of said respective reactive compounds bonded onto preselected areas of an inert substrate carrier to form a substrate carrier sensitized at each of a plurality of preselected areas with a respective one of a plurality of immobilized reactive compounds interspaced by areas of said substrate carrier free of said compounds to permit said substances and said competing compounds in said mixture to competitively conjugate with their respective reactive compounds immobilized on said substrate carrier;

(c) washing excess of said sample from each of said preselected areas of said substrate carrier in a common washing treatment to obtain an exposed substrate carrier;

(d) simultaneously treating each of said plurality of areas of said exposed substrate carrier in a common treatment step with a tracer-labelled developer reactive with the competing compound conjugates to deposit on each of said preselected areas a tracer (reporter) substance at a concentration proportional to said competing compound conjugate thereon, and simultaneously washing each of said preselected areas of the developed substrate carrier in a common washing step (prior to said measuring step); and (e) measuring the concentrations of said tracer substances on the preselected areas of said carrier.

11. The method of claim 10 including the step of preparing the sensitizied carrier by reacting each of a plurality of said respective reactive compounds with said carrier to bind each of said reactive compounds onto a preselected area of said carrier interspaced by areas of said substrate carrier free of said compounds.

12. The method of claim 10 wherein said tracer-labelled developer is a radioactive substance.

13. The method of claim 10 including the steps for calibrating the sensitized carrier by exposing preselected calibration areas of said sensitized carrier to a plurality of dilutions of a reference solution comprising mixtures of known concentrations of each of the substances to be analyzed.

14. The method of claim 10 wherein said tracer-labelled developer is an enzymatic substance.

15. The method of claim 14 wherein a chromophore enzyme-substrate derivative is also added in said measuring step to precipitate a chromogenic substance on said preselected areas from said chromophore enzyme-substrate derivative cleaved by said enzymatic derivative.

16. The method of claim 15 wherein said tracer-labelled substances are chromophore derivatives of said substances.

17. The method of claim 16 wherein said chromophore derivatives are fluorophores.

* * * * *